United States Patent [19]

McMillan

[11] 4,234,683
[45] Nov. 18, 1980

[54] BETA-LACTAMASE DIAGNOSTIC PRODUCT AND METHOD

[76] Inventor: William A. McMillan, 2981 Magliocco Dr., Apt. 2, San Jose, Calif. 95128

[21] Appl. No.: 963,910

[22] Filed: Nov. 24, 1978

[51] Int. Cl.$^3$ .......................... C12Q 1/34; C12Q 1/36; C12Q 1/04
[52] U.S. Cl. ........................................ 435/18; 435/24; 435/29; 435/32; 435/34; 252/408
[58] Field of Search ....................... 435/18, 23, 24, 29, 435/32, 34, 243, 253, 805, 810, 851, 871; 252/408; 23/230 B

[56] References Cited

U.S. PATENT DOCUMENTS

| | | | |
|---|---|---|---|
| 2,601,350 | 6/1952 | Welch | 435/30 |
| 3,616,251 | 10/1971 | Linoti | 435/24 X |
| 3,830,700 | 8/1974 | O'Callaghan et al. | 435/18 |
| 4,066,509 | 1/1978 | Ceska | 435/24 X |

OTHER PUBLICATIONS

R. P. Novick, Biochemistry Journal, vol. 83, pp. 236–240, 1962.
C. Thornsberry et al., Antimicrobial Agents and Chemotherapy, vol. 6, No. 5, pp. 653–654, 1974.
James H. Jorgensen et al., Antimicrobial Agents and Chemotherapy, vol. 11, No. 2, pp. 1087–1088, 1977.
Tolu Odugbemi et al., British Medical Journal, p. 500, 1977.
B. Wesley Catlin, Antimicrobial Agents and Chemotherapy, vol. 7, No. 3, pp. 265–270, 1975.

Primary Examiner—Robert J. Warden
Attorney, Agent, or Firm—Phillips, Moore, Weissenberger, Lempio & Majestic

[57] ABSTRACT

A diagnostic product and method are provided for rapid, sensitive and reproducible screening of penicillin resistance in bacteriological species such as *Neisseria gonorrhoeae* and *Haemophilus influenzae*. The diagnostic product and method of the present invention are utilized with aqueous solutions of iodine. The product includes four components; a porous support; a starch; a substrate such as penicillin and, a nucleophilic reagent. Preferred embodiments include a particular nucleophilic reagent which provides assay results in about 10 to about 30 seconds. The best mode contemplated for the diagnostic product is an embodiment in the form of a kit.

20 Claims, 1 Drawing Figure

4,234,683

BETA-LACTAMASE DIAGNOSTIC PRODUCT AND METHOD

BACKGROUND

1. Field of the Invention

This invention relates to diagnostic products and methods which utilize iodine-starch indicator systems in assays for reaction products from beta-lactamase catalyzed penicillin or penicillin-like substrates.

2. Prior Art

The penicillins and cephamycins have proven to be among the most preferred and generally useful antibiotics in the medical arsenal. It is of considerable conern, therefore, that recently several bacteriological species hitherto usefully and indeed preferably treated by administration of penicillins or cephamycins have been found to display decreased susceptibility to these antibiotics. A certain portion of such resistant bacteriological species have been shown to produce the enzyme beta-lactamase (at times referred to as penicillinase). For example, resistance to ampicillin by *Haemophilus influenzae* is reported and discussed by Thornsberry et.al. in *Antimicrobial Agents and Chemotherapy*, Vol. 6 No. 5 pages 653–654 (1974). *Haemophilus influenzae* causes acute bacterial meningitis of particular virulence in children. Another bacteria, *Neisseria gonorrhoreae*, has also been found to have penicillin resistant strains.

The penicillins and cephamycins probably inhibit bacteria by preventing cross-linking of the peptide chains necessary in formation of the bacterial cell walls. Both the penicillin and cephamycins include a 4-membered ring, denominated as the beta-lactam ring, which contains peptide bond as the functional site for the inhibitory function of penicillins and cephamycins. When bacteria are inhibited in their cell-wall synthesis, they are vulnerable to adverse environmental conditions or their own autolytic enzymes. When bacteriological species produce beta-lactamase, the beta-lactamase catalyzes a reaction in which the beta-lactam ring is ruptured. Hydrolysis results which causes destruction of the inhibitory capability of the penicillins and cephamycin substrates.

When such substrates have undergone beta-lactam ring cleavage (rupture of the peptide bond) the resulting structure is hereinafter throughout referred to for convenience as a penicilloic acid type moiety. Penicilloic acid type moieties contain a non-acylated amino group which is capable of reducing iodine to iodide.

Recently, the prior art has described B-lactamase production assay techniques which depend upon the interaction of a localized reductive reaction of iodine to iodide by penicilloic acid type moieties with a starch-iodine indicator system.

Among these reports, Jorgensen et.al. *Antiomicrobial Agents in Chemotherapy*, Vol. 11, No: 2, pages 1087–1088 (1977) discloses paper strips which have been impregnated with starch and potassium penicillin G as substrate. The impregnation is by immersion of the paper strips in a 0.2 wt.% starch and 1 wt.% penicillin solution. These strips are then moistened with either Gram's iodine (0.013 M iodine) or Lugol's iodine (as usually used, 0.039 M iodine). When colonies of bacteria are applied, a pale discolorization in the area of application provides a presumption of beta-lactamase production (iodine reduction to iodide).

Another literature report, Odugbemi et.al., *British Medical Journal*, pg. 500 (1977), teaches that various paper strips of unknown starch concentrations are soaked in a phosphate-buffered saline solution containing 10 wt.% of benzyl penicillin substrates. Bacterial colonies are then applied to the paper strips, incubated and then flooded with Gram's iodine diluted 1 to 2 (0.007 M iodine). A pale discolorization, read five minutes after iodine flooding, provides a presumption of beta-lactamase.

Neither the Jorgensen nor the Odugbemi paper strips and techniques have been found to provide satisfactory assay results. These prior products and techniques are not sufficiently sensitive or reproducible for large scale, hospital screening and/or public health use.

The Jorgensen teachings have been found deficient primarily in two respects. First, the low concentration of substrate taught by Jorgensen is believed to result in unfavorable kinetics for enzyme activity so that maximum reactive velocity is not attained, or the actual reaction velocity is not a direct function of the enzyme concentration. Second, the undiluted use of Gram's, and particularly the use of Lugol's, iodine presents problems in that development of decolorization in the area of bacteria application is frequently masked by excess iodine (in relation to the amount of penicilloic acid type moiety produced in a reasonable period of time). Thus, despite the application of known beta-lactamase producing bacteriological strains (as confirmed by other methods), the Jorgensen paper strip and technique frequently results in no discernible fading, overly slow, or only slight fading in the area of bacteria application.

The Odugbemi teachings also have been found unsatisfactory in several aspects. First, colonies of the bacteriological species must be incubated upon the paper strips in the presence of substrate. In large scale screening, such incubation is not convenient. Second, dilution of the Gram's or Lugol's iodine solution is inconvenient, since these solutions are stock concentrations for a multitude of purposes, and, more importantly, dilution results in a background color which is too pale for sensitive contrast with the area of bacteria application. Also, the lack of control over starch concentrations of the Odugbemi strips creates difficulty in reproducibility.

The present invention is directed to overcome one or more of the problems of the prior art assay products and techniques.

SUMMARY OF THE INVENTION

The present invention is a diagnostic product useful for assaying beta-lactamase producing bacteriological species and is designed to be used in combination with an aqueous solution of iodine. The diagnostic product comprises starch, a substrate, and a nucleophilic reagent, which are to be absorbed upon a porous support. The substrate includes a beta-lactam ring. Two preferred embodiments of the inventive diagnostic product are disclosed.

In another sense, the present invention is an improved assay method for distinguishing bacteriological species with resistance to penicillin and penicillin like materials in the presence of an aqueous iodine solution.

DETAILED DESCRIPTION OF THE PREFERRED EMBODIMENTS

Figure 1:
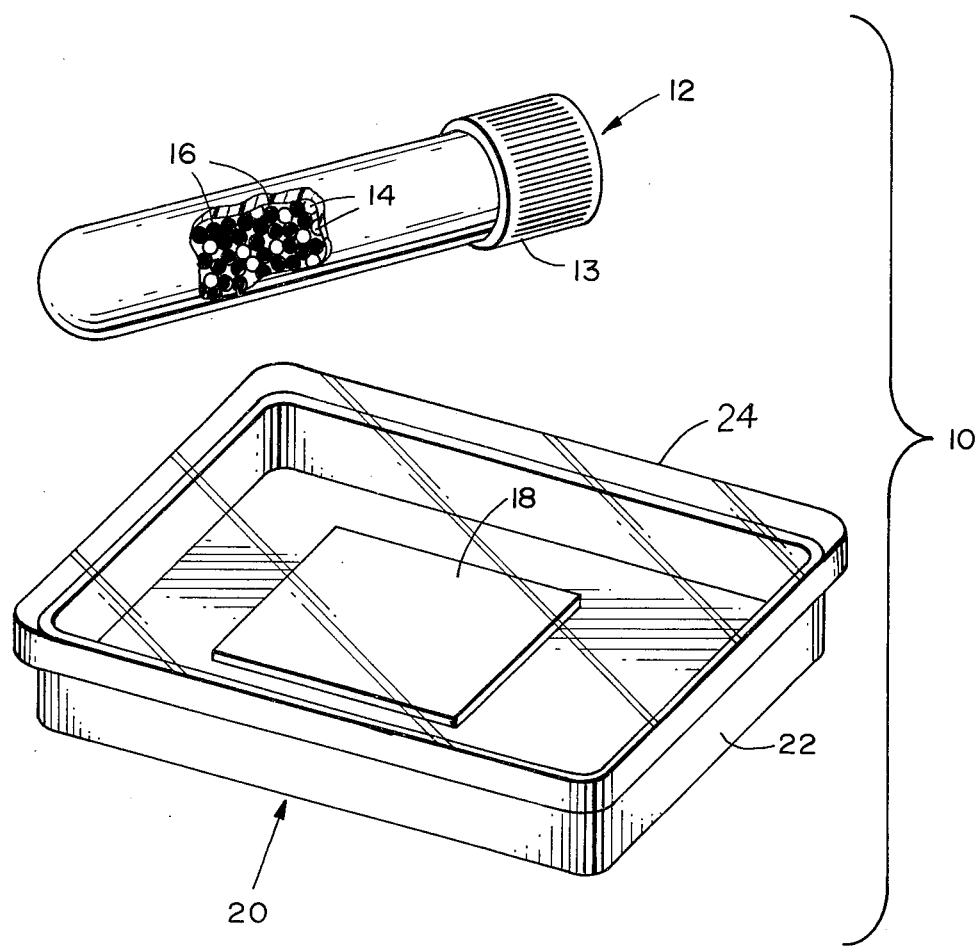
FIG. 1 illustrates a perspective of an embodiment in accordance with the present invention, with a portion broken away.

The diagnostic product of the present invention comprises four components, and is useful in combination with an aqueous solution of iodine. The four components of the present invention are a porous support, a substrate, a starch and a nucleophilic reagent.

The best mode contemplated for practice of the embodiments of the present invention is to utilize an aqueous solution of iodine in combination therewith. As is well known, pure crystalline iodine is very insoluble in water, but is soluble in an aqueous solution containing iodide ions. The source of iodide ions is usually provided by potassium iodide. A preferred aqueous solution of iodine for the present invention is known as Gram's iodine which has an iodine concentration of about 0.013 M iodine. Aqueous solutions of iodine with a range of iodine from about 0.010 M to about 0.015 M are most suitable.

Support

The support component of the present invention should be porous to permit absorption of the starch, substrate and nucleophilic reagent thereupon. It is preferred that the support be insoluble and inert under the temperature and pH conditions believed to be optimal for the assays.

The support provides a template for the localized application and subsequent visual observation of the effect of the bacteriological species being assayed, and yet does not itself enter into the reactions during the assays. Suitable materials for the support are, for example, cellulose, agar, and agarose. Cellulose materials may conveniently be in the form of strips, whereas agar and agarose materials may be in the form of slabs, or may be jelled upon a manipulating member such as glass slide.

An excellent, readily available and inexpensive material for the support is simply filter paper, preferably of medium thickness and porosity.

Substrate

The substrate for the enzyme of the assay includes a beta-lactam ring upon which the beta-lactamase enzyme, if present, will act. The beta-lactam ring has the structure:

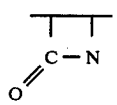

The enzyme beta-lactamase catalyzes a hydrolysis reaction which opens the peptide bond.

The beta-lactam ring of the substrate structure may be condensed to either a five-membered thiazole ring, preferably thiazolidine, to provide the condensed structure:

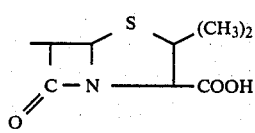

or to a dihydrothiazine ring. However, substrates which take the form of the thiazolidine ring condensed to the beta-lactam ring are readily available and less expensive than substrates which include the dihydrothiazine ring (such as the cephamycins), and hence the former are preferred.

When one further builds the structure by incorporating a substituted amide therewith, the substrate would have the following penicillin analog structure:

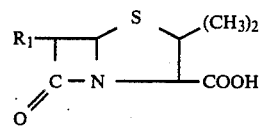

wherein $R_1$ is a substituted amide of an aromatic carboxylic acid.

Most preferred are penicillin substrates with the structure:

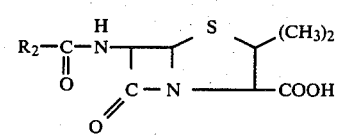

wherein the $R_2$ group may be benzyl (penicillin G), phenoxylmethyl (penicillin PVO, alpha-amino benzyl (ampicillin), d-carboxybenzyl (Carbenicillin) or dimethoxyphenyl (Methicillin). A bulky $R_2$ group, particularly the dimethoxyphenyl group of Methicillin, may tend to inhibit the beta-lactamase, and therefore the most preferred $R_2$ group for a substrate of the present invention is benzyl.

Approximately 1 to 10 colonies are a useful quantity of the bacteriological species to be applied to the support. An excess of substrate with respect to the bacteriological species is impregnated upon the support to ensure that the beta-lactamase activity will result in a maximum velocity of the hydrolysis reaction, represented below by equation (1) wherein equation (1) represents a penicilloic acid type moiety at the reaction product, or that the actual velocity of the hydrolysis reaction is a direct function of the enzyme concentration.

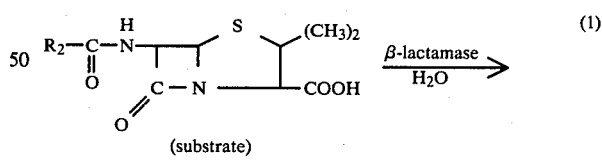

(substrate)

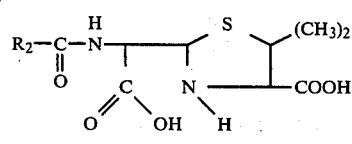

(reaction product)

The quantity of substrate for providing an excess of substrate if from about 4 to about 20 wt.% substrate which has been dissolved in the aqueous solution in which the support is exposed, or immersed. More preferably, from about 12 to about 15 wt.% substrate is dissolved in an aqueous solution in which the support is to be exposed.

Starch

As is well known, starch and iodine form a blue colored complex in an aqueous solution. More precisely, iodine and the water soluble fraction of starch, amylose, form the blue colored complex, however, starch shall be the term used hereinthroughout. The source of the iodine molecule for such complexing is form the aqueous solution of iodine previously described, and is presented below by equation (2).

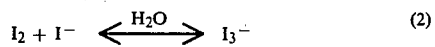

$$I_2 + I^- \xrightleftharpoons{H_2O} I_3^- \quad (2)$$

The tri-iodide has a brownish color in solution.

If a sufficient amount of a reducing agent is present in an aqueous iodine solution in the presence of starch to irreversibly reduce all of the iodine to iodide, then the blue color due to the starch-iodine complex will change to colorless, as represented below by the two different reactions illustrated by equation (3).

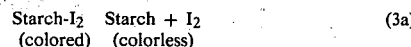

$$\text{Starch-I}_2 \rightarrow \text{Starch} + I_2 \quad (3a)$$
(colored) (colorless)

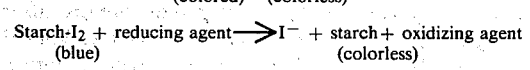

$$\text{Starch-I}_2 + \text{reducing agent} \rightarrow I^- + \text{starch} + \text{oxidizing agent} \quad (3b)$$
(blue) (colorless)

The prior art has utilized the reactions represented by equation (3) as follows: substrates such as the penicillins, when catalyzed by the enzyme beta-lactamase in the presence of water, form reaction products which are organic reducing agents. These organic reducing agents, of which penicillinoic acid is an example and called generally herein penicilloic acid type moieties, include an unshared pair of electrons on the nitrogen of the opened beta-lactam ring which function to reduce iodine to iodide. The penicilloic acid type moiety is believed to be irreversibly oxidized with the evolution of carbon dioxide gas.

Further, for sensitive, reproducible assays utilizing localized production and reaction of penicilloic acid type moieties, it is important that the background area of the support be of sufficiently intense color from the starch-iodine complex to provide a good contrast with the area of bacteriological species application (which will fade in color if beta-lactamse is present). It has been found that immersion, or exposure, of the support component of the present invention in a solution containing from about 0.20 to about 1.0 weight % starch, provides that sufficient starch is absorbed upon the support for subsequent colorization when flooded with an aqueous iodine solution. More preferably, the starch solution is from about 0.25 to about 0.30 wt.% in which the support is immersed, or exposed. In the presence of sufficient starch, the iodine concentration in the aqueous iodine solution with which the support is to be flooded is believed to be rate limiting for the background development. Simply ensuring the presence of sufficient starch for an intense background and an excess of substrate for optimizing enzyme substrate kinetics upon the support does not provide consistently reproducible or sensitive assays.

Particularly with certain of the bacteriological species strains shown to produce beta-lactamase by other methods, there has been observed a resistance to fading of color in the area of bacteriological species application where only the support, starch and substrate components are provided as above described. These non-reproducible assay results and the lack of sensitivity is theorized herein to be due in major part to interference by an excess, or uncomplexed, portion of iodine which replaces the iodide, occuring as a result of reaction (3), in the colored starch-iodine complex. Simply diluting the aqueous solution of iodine has not been found effective in preventing such interference, as diluted solutions of iodine, for example with iodine concentrations of from about 0.004 M to about 0.008 M iodine, result in too pale a background for good contrast with the area of bacteriological species application, or very slow, incomplete or inapparent decolorization.

As may be understood from the above discussion, the iodine utilized for indicating the presence of beta-lactamase is involved in a relatively unlocalized, reversible reaction (equation 2), a localized reversible reaction, (equation 3a) and a relatively localized, irreversible reaction (3b). Simultaneously upon the application of bacteriological species, intermediate, localized substrate-enzyme complexes are being formed, substrate is being hydrolyzed therefrom and the reaction product, or penicilloic acid type moiety, is being irreversibly oxidized. It may be said that the irreversible reaction (3b) acts to control the reversible reactions, as reaction rate constants are a partial function of the concentrations of the reactants, so that the equilibrant profile and the reversible reactions in part determined and limited by the penicilloic acid type moiety. However, the chemical kinetics and the topology of these multiple reactions is not well understood, an even theoretical rate equations would involve multiple, simultaneous algebraic equations in terms of several variables (at least one of which, the enzyme concentration, is unknown), and some combination of the various kinetic constants.

The present invention is based upon the surprising discovery that the inclusion of a nucleophilic component, which may function to control the iodine simultaneously with the multiple reactions occuring during the assays, provides a diagnostic product and method with excellent sensitivity and reproducibility of assay results.

Nucleophilic Reagent

As may be observed from the preceeding discussion, the penicilloic acid type moiety formed by beta-lactamase-producing bacteriological species reacting with penicillin or penicillin-like substrates is itself a nucleophilic species by having an unshared pair of electrons on the opened peptide bond of the beta-lactam ring. It is, therefore, particularly surprising that a nucleophilic reagent, separate and distinct from the penicilloic acid type moiety being formed during assay, is a necessary component of the present invention, and that the nucleophilic reagent aids, rather than competively interferes with, assays for beta-lactamase producing bacteriological species.

The nucleophilic reagent component of the present invention is defined as not being a penicilloic acid type moiety and as being capable of donating electrons to iodine. The nucleophilic reagent further must donate electrons to iodine under the temperature and pH conditions believed to be optimal for the assays. The pH optimum for beta-lactamase activity is from about 6.8 to about 7.8, with a pH most preferred of about 7.2. The assays should be performed at temperatures from about 20° C. to about 48° C. Higher temperatures may lead to inactivation of beta-lactamase.

Suitable chemical species for the nucleophilic reagent include water soluble organic compounds with activated benzyl rings for nucleophilic addition of iodine thereto, and water soluble inorganic reducing compounds. Among the organic compounds suitable for the nucleophilic reagent is, for example, tyrosine, which is halogenated endergonically. However, the organic compounds which are suitable for donating electrons to iodine, and hence for controlling the amount of iodine available for reaction with penicilloic acid type moieties, are less preferred than inorganic reducing compounds. Suitable organic compounds have been found to function slowly in the present invention under the temperatures preferred. Hence, the more preferred embodiments of the present invention utilize inorganic reducing compounds.

The most preferred nucleophilic reagent is thiosulfate which donates electrons to iodine in an oxidation-reduction reaction illustrated by equation (4):

$$I_2 + 2S_2O_3^= = 2\,I^- + S_4O_6^= \qquad (4)$$

The concentration of thiosulfate in the solution to which the porous support is exposed is preferably from about 0.05 to about 0.20 M (about 0.5–2.2 wt. %) thiosulfate. More preferred is about 0.10 M thiosulfate. Sodium thiosulfate may be the species for providing the thiosulfate and may be either hydrated or anhdyrous. When thiosulfate is utilized assay results are usually very quickly available, generally in about 10 seconds to about 30 seconds after contact of the diagnostic product with a bacteriological species.

As previously noted, the iodine concentration is believed to be rate limiting for the background development of the support. During flooding with the aqueous solution of iodine, the iodine concentration is in turn being controlled in part by the presence of the nucleophilic reagent. As a result, the background of the preferred color thiosulfate embodiment develops at a fairly uniform rate during the flooding stage. A specific and reproducible background color intensity can be uniformly achieved by flooding the support for an appropriate time, further discussed hereinafter, and simply removing the support from contact with the aqueous iodine solution.

The assaying method for distinguishing bacteriological species with resistance to penicillins and the like comprises an improvement which greatly enhances the sensitivity and reproducibility of assay methods previously known to the prior art. Hitherto it has been known that a porous support may be immersed in an aqueous solution of a starch and a substrate and then dried, or blotted. The prior art has further disclosed application of colonies of bacteriological species to the support followed by exposure of the supports to iodine followed by application of colonies of bacteriological species.

The improvement of the present invention comprises impregnating a porous support, the support including starch and substrate, with a water soluble nucleophilic reagent prior to exposure to the support to iodine. The impregnating step may be most easily accomplished by dissolving the nucleophilic reagent in an aqueous solution including starch and/or substrate, exposing the porous support without the starch and/or substrate being already absorbed to such an aqueous solution, for example, by immersion of the support therein, and retrieving the support thereafter.

It is preferred that the porous support including the starch, substrate and nucleophilic reagent as just described, be next exposed to the aqueous solution of iodine, such as by flooding the support for about 10–60 sec.

The exact time period appropriate for flooding, within the range of about 10–60 seconds, is dependent upon the age and storage conditions of the aqueous iodine solution. Colonies of bacteriological species may then be applied. This ensures that the iodine flooding step does not dilute, or wash away, the bacteriological species or the substrate.

A positive test for bacteriological species with resistance to penicillin or penicillin-like substrate is indicated by visual observation of a decolorization upon the support in the area of bacteriological species application, which decolorization is in contrast to the colored support background. When utilizing thiosulfate as the nucleophilic reagent, one may achieve an indication of positive test results within less than about one minute, and in many instances in as little time as 10 seconds.

A preferred additional step, particularly where screening of a plurality of specimens is desired, is to provide an exposure of the impregnated support, after flooding but prior to application of the bacteriological species, to iodine vapor. Such exposure may comprise, for example, placing the impregnated and flooded support within a closed system in which is also enclosed a small pool of iodine solution. The atmosphere of such system thus contains some iodine vapor. Such an exposure is preferred, as the background color of the support slowly fades. The exposure of the support to iodine vapor, however, has been found to significantly retard this fading, and hence the person conducting the assays may conveniently handle a plurality of specimens, yet insure consistent, reproducible results amongst them all.

The following example illustrate embodiments in accordance with the present invention.

EXAMPLE I

Filter papers of medium thickness an porosity, for example, Whatman No. 40 (available from W. R. Balstan Co., Englewood, New Jersey) and S & S 591-A or 598 (available from Schleicher and Schuell, Keene New Hampshire) were individually immersed in one of seven different solutions (1–7) for 1 minute then retrieved drained, dried and cut into strips of about 1 centimeter by 8 centimeters. The seven solutions in which the filter papers, or supports, were immersed were as follows:

| Solution # | Solution Composition |
|---|---|
| 1 | 12 wt. % Penicillin G (phosphate buffered, pH 6.8–7.4) |
| | 0.25 wt. % starch |
| | 0.05 M $Na_2S_2O_3 \cdot 5H_2O$ |
| | remainder $H_2O$ |
| 2 | 12 wt. % Penicillin G (phosphate buffered, pH 6.8–7.4) |
| | 0.25 wt. % starch |
| | 0.10 M $Na_2S_2O_3 \cdot 5H_2O$ |
| | remainder $H_2O$ |
| 3 | 12 wt. % Penicillin G (phosphate buffered, pH 6.8–7.4) |
| | 0.50 wt. % starch |
| | 0.05 M $Na_2S_2O_3 \cdot 5H_2O$ |
| | remainder $H_2O$ |
| 4 | 12 wt. % Penicillin G (phosphate buffered, pH 6.8–7.4) |
| | 0.50 wt. % starch |
| | 0.10 M $Na_2S_2O_3 \cdot 5H_2O$ |

| Solution # | Solution Composition |
|---|---|
| | remainder H$_2$O |
| 5 | 12 wt. % Penicillin G (phosphate buffered, pH 6.8–7.4) |
| | 0.50 wt. % starch |
| | 0.15 M Na$_2$S$_2$O$_3$ . 5H$_2$O |
| | remainder H$_2$O |
| 6 | 12 wt. % penicillin G (phosphate buffered, pH 6.8–7.4) |
| | 0.75 wt. % starch |
| | 0.15 M Na$_2$S$_2$O$_3$ . 5H$_2$O |
| | remainder H$_2$O |
| 7 | 12 wt. % penicillin G (phosphate buffered, pH 6.8–7.4) |
| | 1.00 wt. % starch |
| | 0.20 M Na$_2$S$_2$O$_3$ . 5H$_2$O |
| | remainder H$_2$O |

The retrieved supports from each of the solutions (1–7) were then flooded with Gram's iodine for about 5 seconds, drained and blotted. One to ten colonies of one of several beta-lactamase producing *N. gonorrhoea* were applied lightly in a circular manner to the supports of each of the solutions (1–7). Visual observation of the supports were made with respect to background intensity and reaction speed. Background intensity was determined on a scale from 0 to 3+ wherein: 0 indicates no color, or irregular color; 1+ indicates slight brown color; 2+ indicates brown without or with slight bluish tinge; and, 3+ indicates dark brown with a definite bluish tinge. Background intensity values of 2+ to 3+ are considered fully satisfactory. The reaction speed was determined on a scale of 0 to fast wherein: 0 indicates no discernable discolorization after application of the organism up to 5 minutes; slow indicates greater than 30 seconds for decolorization; medium indicates 10 to 30 seconds for decolorization; and, fast indicates less than 10 seconds for decolorization. A reaction speed of medium to fast was considered fully satisfactory, with a reaction speed of slow being acceptable, but less preferred.

| Supports from Soln. # | Background Intensity | Reaction Speed |
|---|---|---|
| 1 | 2+–3+ | medium–fast |
| 2 | 2+ | fast |
| 3 | 3+ | slow |
| 4 | 2+–3+ | slow |
| 5 | 1+–2+ | slow–medium |
| 6 | 2+–3+ | slow |
| 7 | 2+–3+ | slow |

The above data illustrates that embodiments in accordance with the present invention provide a diagnostic product with good background color development for reproducibility. Solutions (3–7) provide acceptable reaction speed; however, solutions (1) and (2) provide a more preferred reaction speed of 30 seconds or less, solution (2) being most preferred with a reaction speed of less than 10 seconds.

EXAMPLE II

Four different solutions (8–11) were prepared and used for immersion of filter papers as described in Example I. These four solutions were as follows:

| Solution # | Solution Composition |
|---|---|
| 8 | 12 wt. % Penicillin G (phosphate buffered, pH 6.8–7.4) |
| | 0.25 wt. % starch |
| | 0.25 M Na$_2$S$_2$O$_3$ . 5H$_2$O |
| | remainder H$_2$O |
| 9 | 12 wt. % Penicillin G (phosphate buffered pH 6.8–7.4) |
| | 0.05 wt. % starch |
| | 0.25 M Na$_2$S$_2$O$_3$ . 5H$_2$O |
| | remainder H$_2$O |
| 10 | 12 wt. % Penicillin G (phosphate buffered pH 6.8–7.4) |
| | 0.75 wt. % starch |
| | 0.05 M Na$_2$S$_2$O$_3$ . 5H$_2$O |
| | remainder H$_2$O |
| 11 | 12 wt. % Penicillin G (phosphate buffered, Ph 6.8–7.4) |
| | 1.00 wt. % starch |
| | 0.05 M Na$_2$S$_2$O$_3$ . 5H$_2$O |
| | remainder H$_2$O |

The retrieved supports were then treated as in Example I and visual observation made, the data as follows:

| Supports from Solution # | Background Intensity | Reaction Speed |
|---|---|---|
| 8 | 0 | 0 |
| 9 | 0 | 0 |
| 10 | 3+ | 0–slow |
| 11 | 3+ | 0–slow |

The above data illustrates that diagnostic products which include the presence of too much nucleophilic reagent (solutions 8 and 9) result in no background color development. It is believed that solutions 8 and 9 represent situations where the nucleophilic reagent is functioning to successfully compete with and block formation of the starch-iodine complex. Solutions 10 and 11 illustrate a somewhat converse situation, wherein good background color is developed but insufficient of the nucleophilic reagent is present relative the amount of starch for providing acceptably rapid positive assay results.

EXAMPLE III

Beta-lactamase producing strains of bacteriological species were diluted in six different dilution ratios by mixing with bacteriological species strains known to be non-beta-lactamase producing. These diluted mixtures were then incubated upon a chocolate agar medium for 24 hours. One non-diluted, beta-lactamase producing strain was incubated as a control. Dilutions were made by establishing standard turbidity readings of both the enzyme-producing and non-enzyme producing strains. One inoculating loopful each of the 7 bacteriological species preparations was then applied to each of supports prepared in accordance with the present invention. That is, these supports were prepared as described above in Example I, but wherein another 7 solutions (12–18) were prepared in which the supports were immersed for absorbance of the substrate, starch and nucleophilic reagent as follows:

| Solution # | Solution Composition |
|---|---|
| 12 | 4 wt. % Penicillin G (phosphate buffered, pH 6.8–7.4) |
| | 0.25 wt. % starch |
| | 0.10 M Na$_2$S$_2$O$_3$ . 5H$_2$O |

| Solution # | Solution Composition |
|---|---|
| | remainder H$_2$O |
| 13 | 6 wt. % Penicillin G (phosphate buffered, pH 6.8-7.4) |
| | 0.25 wt. % starch |
| | 0.10 M Na$_2$S$_2$O$_3$ . 5H$_2$O |
| | remainder H$_2$O |
| 14 | 8 wt. % Penicillin G (phosphate buffered, pH 6.8-7.4) |
| | 0.25 wt. % starch |
| | 0.10 M Na$_2$S$_2$O$_3$ . 5H$_2$O |
| | remainder H$_2$O |
| 15 | 10 wt. % Penicillin G (phosphate buffered, pH 6.8-7.4) |
| | 0.25 wt. % starch |
| | 0.10 M Na$_2$S$_2$O$_3$ . 5H$_2$O |
| | remainder H$_2$O |
| 16 | 12 wt. % Penicillin G (phosphate buffered, pH 6.8-7.4) |
| | 0.25 wt. % starch |
| | 0.10 M Na$_2$S$_2$O$_3$ . 5H$_2$O |
| | remainder H$_2$O |
| 17 | 16 wt. % Penicillin G (phosphate buffered, pH 6.8-7.4) |
| | 0.25 wt. % starch |
| | 0.10 M Na$_2$S$_2$O$_3$ . 5H$_2$O |
| | remainder H$_2$O |
| 18 | 20 wt. % Pencillin G (phosphate buffered, pH 6.8-7.4) |
| | 0.25 wt. % starch |
| | 0.10 M Na$_2$S$_2$O$_3$ . 5H$_2$O |
| | remainder H$_2$O |

Visual observations of the supports after iodine treatment and application of the diluted and control species preparations were made. The supports from solutions (16-18), wherein the substrate concentration in the solutions ranged from about 12 wt.% to about 20 wt.%, provided substantially similar positive tests for beta-lactamase production within one minute with dilutions of up to about one part beta-lactamase producing strain to about 25 parts non-beta-lactamase producing strain. The remaining solutions (12-15), wherein the substrate concentration in the solution ranged from about 4 wt.% to about 10 wt.%, provided positive tests for beta-lactamase production within one minute, but are dependent upon the dilution ratio of the beta-lactamase producing strains as follows:

| Support from Solution # | Maximum Dilution Ratios for Positive Test Within 1 Minute |
|---|---|
| 12 | non-diluted |
| 13 | 1:10 |
| 14 | 1:15 |
| 15 | 1.15-1:20 |

From the above data, although supports in accordance with the present invention, such as illustrated by solutions (12-15) provide a positive reaction for beta-lactamase production, it is preferred that embodiments of the present invention be prepared from solutions including at least about 12 wt.% substrate for optimal sensitivity.

The best mode contemplated for preparing, shipping and/or storing embodiments of the present invention is whereby the porous support, on which is absorbed the substrate, starch and nucleophilic reagent, is frozen. More preferably, the frozen support is maintained at a temperature of from about −20° C. to about −70° C. This ensures that the frozen supports may be prepared, shipped and/or stored in the frozen condition for up to about 6 months, and simply retrieved from the freezing apparatus when needed for assays.

An alternate best mode for an embodiment of the present invention is whereby the diagnostic product 10 is in kit form. FIG. 1 illustrates this embodiment wherein a moisture tight ampoule 12 encloses two components 14 and 16 of the present invention, that is, encloses the substrate 16 and the nucleophilic reagent 14. The substrate 16, such as penicillin, may be preserved against deterioration by means such as freeze-drying and the nucleophilic reagent 14 in an anhydrous form, is also enclosed therein. The ampoule 12 may be formed of a variety of materials, for example, various plastics or glass and may be sealed for moisture tightness by conventional means such as, for example, cap 13. The kit form further includes a porous support 18 on which the starch component has been absorbed, the support 18 thereafter having been dried, and means 20 for holding the support 18, for adding water thereof, and for adding the substrate 16 and nucleophilic reagent 14 thereto from ampoule 12. Means 20 may be, for example, a tray 22. Additionally, means 20 may include a lid 24, illustrated for convenience as transparent in FIG. 1. When means 20 includes both lid 24 and tray 22, the person conducting the assays may utilize means 20 to expose the flooded and impregnated support to iodine vapor, as previously discussed. This kit form is particularly useful for shipment to and storage by clinics in areas of the world where freezing facilities are not available.

While the invention has been described in connection with specific embodiments thereof, it will be understood that it is capable of further modification, and this application is intended to cover any variations, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

What is claimed is:

1. A diagnostic product useful for sensitive, reproducible assays of microorganisms which produce beta-lactamase comprising:
a porous support on which is absorbed a substrate component, a starch component and a water-soluble thiosulfate component, the substrate component having a beta-lactamase ring.

2. A diagnostic product as in claim 1 wherein the beta-lactam ring of the substrate component is condensed to a ring selected from the group consisting of thiazolidiene and dihydrothiazine.

3. A diagnostic product as in claim 2 wherein the substrate component has the structure

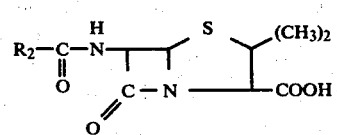

and R$_2$ is selected from the group consisting of benzyl, phenoxylmethyl, α-aminobenzyl, α-carboxybenzyl and dimethyoxyphenyl.

4. The diagnostic product as in claim 3 wherein R$_2$ is benzyl.

5. A diagnostic product as in claim 1 wherein the substrate has the structure:

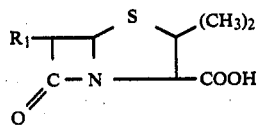

wherein $R_1$ is a substituted amide of an aromatic carboxylic acid.

6. The diagnostic product as in claim 1 wherein said porous support has said substrate component, said starch component and said thiosulfate component upon the support in a weight ratio of substrate to starch to thiosulfate of about 4–20/0.2–1.0/0.5–2.2.

7. The diagnostic product of claim 1 wherein the support is selected from the group consisting of cellulose, agar, and agarose.

8. The diagnostic product of claim 1 wherein the support is frozen.

9. The diagnostic product as in claim 8 wherein the frozen support is at a temperature from about $-20°$ C. to about $-70°$ C.

10. A diagnostic product, useful for assaying for microorganisms which produce beta-lactamase, said product formed by the steps comprising:
absorbing upon a porous support a substrate component, a starch component, and a thiosulfate component, the absorbing by exposing the support to an aqueous solution in which the components are dissolved, the aqueous solution including from about 4 to about 20 wt.% of the substrate component, from about 0.2 to about 1.0 wt.% of the starch component and from about 0.05 to about 0.20 M of the thiosulfate component, wherein the substrate has the structure

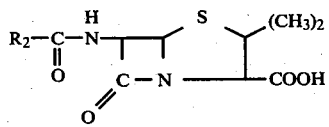

and $R_2$ is selected from the group consisting of benzyl, phenoxylmethyl, α-aminobenzyl, α-carboxybenzyl, and dimethyloxyphenyl; and;

retrieving the porous support from the aqueous solution.

11. The diagnostic product as in claim 10 further comprising freezing the porous support after the retrieving step.

12. The diagnostic product as in claim 11 wherein the freezing is at a temperature from about $-20°$ C. from about $-70°$ C.

13. In an assaying method for distinguishing microorganisms with resistance to an antiobiotic, the antibiotic including a beta-lactam ring, wherein a starch and the antibiotic are absorbed upon a porous support, the porous support is flooded with an aqueous solution of iodine, and a microorganism culture is applied to the porous support, the improvement comprising:
impregnating the support with a water soluble thiosulfate compound, the impregnating prior to the application of the microorganism culture to the support.

14. The method as in claim 13 wherein the impregnating comprises:
dissolving the thiosulfate compound in an aqueous solution, exposing the support thereto, and retrieving and draining the support.

15. The method as in claim 14 wherein the aqueous solution to which the support is exposed further includes said starch and said substrate dissolved therein for absorption upon said support.

16. The method as in claim 13 further comprising: freezing the support prior to flooding, the freezing at a temperature from about $-20°$ C. to about $-70°$ C.

17. A diagnostic kit useful for assaying penicillin resistant bacteriological species, comprising:
a moisture tight ampoule, the ampoule enclosing two components, the first component comprising a freeze-dried penicillin and the second component comprising an anhydrous water soluble thiosulfate compound; and, a porous support having starch absorbed thereon.

18. The diagnostic kit as in claim 17 wherein the second component comprises anhydrous sodium thiosulfate.

19. The diagnostic kit as in claim 17 including a means for holding the supports to which water and the contents of the ampoule can be added thereto.

20. The diagnostic kit as in claim 19 wherein said means is a tray and further includes a lid.

* * * * *

UNITED STATES PATENT AND TRADEMARK OFFICE
CERTIFICATE OF CORRECTION

PATENT NO. : 4,234,683
DATED : November 18, 1980
INVENTOR(S) : William A. McMillan It is certified that error appears in the above-identified patent and that said Letters Patent are hereby corrected as shown below:

Column 10, line 9, "0.05" should be --0.50--.

Signed and Sealed this

Fourteenth Day of April 1981

[SEAL]

Attest:

RENE D. TEGTMEYER

Attesting Officer    Acting Commissioner of Patents and Trademarks